US010626468B2

United States Patent
Zhang et al.

(10) Patent No.: US 10,626,468 B2
(45) Date of Patent: Apr. 21, 2020

(54) **PRIMER PAIR, KIT AND METHOD FOR DETECTING *EHRLICHIA CANIS***

(71) Applicant: Delta Electronics Int'l (Singapore) Pte Ltd, Singapore (SG)

(72) Inventors: Yong Zhang, Singapore (SG); Chih-Yu Chao, Singapore (SG); Kah Sin Loh, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 226 days.

(21) Appl. No.: 15/678,802

(22) Filed: Aug. 16, 2017

(65) Prior Publication Data
US 2018/0080066 A1   Mar. 22, 2018

Related U.S. Application Data

(60) Provisional application No. 62/393,204, filed on Sep. 12, 2016.

(30) Foreign Application Priority Data

Aug. 11, 2017 (SG) .............................. 10201706580Q

(51) Int. Cl.
  *C12P 19/34* (2006.01)
  *C12Q 1/689* (2018.01)
(52) U.S. Cl.
  CPC .................................. *C12Q 1/689* (2013.01)
(58) Field of Classification Search
  CPC ...................................................... C12Q 1/689

USPC ........................................................ 435/91.2
See application file for complete search history.

(56) References Cited

U.S. PATENT DOCUMENTS

| 6,923,963 | B2 | 8/2005 | Rikihisa et al. |
| 7,407,770 | B2 | 8/2008 | O'Connor, Jr. |
| 7,888,054 | B2 | 2/2011 | Krah, III et al. |
| 7,888,491 | B2 | 2/2011 | Rikihisa et al. |
| 8,492,103 | B2 | 7/2013 | Thomas et al. |
| 2003/0185849 | A1* | 10/2003 | Walker .................. C07K 14/29 424/190.1 |
| 2005/0170341 | A1 | 8/2005 | Stich et al. |

FOREIGN PATENT DOCUMENTS

CN          103060468          4/2013

OTHER PUBLICATIONS

Kongklieng et al., Southeast Asian J. Trop. Med. Public Health, 45 (5), 1149-11-56, Sep. 2014.*

* cited by examiner

*Primary Examiner* — Cynthia B Wilder

(74) *Attorney, Agent, or Firm* — Kirton McConkie; Evan R. Witt

(57) ABSTRACT

Primer pair, kit and method for detecting *Ehrlichia canis* are disclosed. The primer pair includes a forward primer and a reverse primer, and the kit includes the primer pair and a probe. The forward primer has a sequence of SEQ ID NO: 1, the reverse primer has a sequence of SEQ ID NO: 2, and the probe has a sequence of SEQ ID NO: 3.

3 Claims, 4 Drawing Sheets

Specification includes a Sequence Listing.

```
  1   ATGAATTGCA AAAAAATTCT TATAACAACT GCATTAATGT CATTAATGTA CTATGCTCCA
 61   AGCATATCTT TTTCTGATAC TATACAAGAC GATAACACTG GTAGCTTCTA CATCAGTGGA
121   AAATATGTAC CAAGTGTTTC ACATTTTGGT GTTTTCTCAG CTAAAGAAGA AAGAAACTCA
181   ACTGTTGGAG TTTTTGGATT AAAACATGAT TGGAATGGAG GTACAATATC TAACTCTTCT
241   CCAGAAAATA TATTCACAGT TCAAAATTAT TCGTTTAAAT ACGAAAACAA CCCATTCTTA
301   GGGTTTGCAG GAGCTATTGG TTATTCAATG GGTGGCCCAA GAATAGAACT TGAAGTTCTG
361   TACGAGACAT TCGATGTGAA AAATCAGAAC AATAATTATA GAACGGCGC ACACAGATAC
421   TGTGCTTTAT CTCATCATAG TTCAGCAACA AGCATGTCCT CCGCAAGTAA CAAATTTGTT
481   TTCTTAAAAA ATGAAGGGTT AATTGACTTA TCATTTATGA TAAATGCATG CTATGACATA
541   ATAATTGAAG GAATGCCTTT TTCACCTTAT ATTTGTGCAG GTGTTGGTAC TGATGTTGTT
601   TCCATGTTTG AAGCTATAAA TCCTAAAATT TCTTACCAAG GAAAACTAGG ATTAGGTTAT
661   AGTATAAGTT CAGAAGCCTC TGTTTTTATC GGTGGACACT TTCACAGAGT CATAGGTAAT
721   GAATTTAGAG ACATCCCTGC TATGGTTCCT AGTGGATCAA ATCTTCCAGA AAACCAATTT
781   GCAATAGTAA CACTAAATGT GTGTCACTTT GGTTTAGAAC TTGGAGGAAG ATTTAACTTC
841   TGA     - SEQ ID NO: 4
```

FIG. 1

| Name | Sequence | |
|---|---|---|
| Forward Primer | 5'-ATTAATGTACTATGCTCCAAG-3' | (SEQ ID NO: 1) |
| Reverse Primer | 5'-GTTGAGTTTCTTTCTTCTTTAG-3 | (SEQ ID NO: 2) |
| Probe | 5'-ACTATACAAGACGATAACACTGGTAGC-3' | (SEQ ID NO: 3) |

FIG. 2

PRIMER PAIR, KIT AND METHOD FOR DETECTING *EHRLICHIA CANIS*

CROSS-REFERENCE TO RELATED APPLICATION

This application claims the benefit of U.S. Provisional Application Ser. No. 62/393,204 filed on Sep. 12, 2016, and claims the priority to Singapore Patent Application No. 10201706580Q filed on Aug. 11, 2017, the entire contents of which are incorporated herein by reference for all purposes.

FIELD OF THE INVENTION

The present invention relates to a quick diagnosis of *Ehrlichia canis*, and more particularly to primer pair, kit and method for detecting *Ehrlichia canis*.

BACKGROUND OF THE INVENTION

*Ehrlichia canis* is a small, rod shaped, intracellular, tick-transmitted, Gram-negative, α-proteobacterium transmitted by the brown dog tick, *Rhipicephalus sanguineus*. It resides as a microcolony inside an intracellular vacuole that is membrane-lined and is mainly within monocytes and macrophages of mammalian hosts. The genus *Ehrlichia* is closely related to the genera *Rickettsia, Anaplasma*, and *Wolbachia*. They all share the similar intracellular structure.

*Ehrlichia canis* was first discovered in Algeria in 1935 and has now been known to have spread all over the United States, Europe, South America, and Asia. It causes ehrlichiosis in dogs, which is an infection transmitted by the tick. Infected dogs that are not treated can become asymptomatic carriers of the disease for years and eventually die from massive hemorrhage. Ehrlichiosis affects dogs and humans as well as other domestic and wild animal species. With global warming, expanding tick habitats and increasing international travel the spread of disease to former non-endemic areas is of great concern.

Ehrlichiosis can have multiple clinical and subclinical presentations making diagnosis challenging. Acute and chronic phases as well as co-infection with other tick-borne pathogens may further complicate therapy. Often, the pathogen cannot be completely eliminated, despite antibiotic treatment and resolution of clinical signs.

Because thrombocytopenia is a relatively consistent finding with these infections, a platelet count is an important screening test. This method of diagnosis lacks sensitivity, because low numbers of organisms make demonstration difficult. Other methods employed for *Ehrlichia canis* diagnosis includes blood smear, serologic diagnosis and molecular diagnosis, but each method has some limitations.

Detection of typical intracellular *E. canis*-morulae on blood smear examination is highly specific for ehrlichiosis. However, this method is time-consuming and not very reliable because morulae are only found in low numbers in blood smears during the acute phase of infection. Microscopy has an estimated sensitivity of 4%.

Serologic diagnosis may be helpful in identifying the presence of antibodies to *Ehrlichia canis*, but may not detect early infections during the acute phase of disease. The limitation of serologic diagnosis is cross-reaction, and the cross-reaction among the *Ehrlichia* spp. and *Ehrlichia* spp. is commonly recognized. Moreover, it is difficult to differentiate between post exposure and present infection.

The most current and best way to diagnose *Ehrlichia canis* is molecular diagnosis, especially by polymerase chain reaction (PCR) testing. PCR, which is more sensitive and specific technique, offers an alternative approach for the diagnosis of *Ehrlichia canis*. For example, the VetPCR *Ehrlichia canis* Detection Kit provided by BioinGentech is used to diagnose *Ehrlichia canis* infection, and it is a very fast, accurate and reliable technique. However, end-point PCR detection method, i.e. gel electrophoresis, should be combined with this diagnostic kit, and the whole procedure will take 3 hours, which is quite labor and time consuming.

Therefore, there is a need of providing an *Ehrlichia canis* diagnosis in order to overcome the above drawbacks.

SUMMARY OF THE INVENTION

An object of the present invention is to provide a primer pair for detecting *Ehrlichia canis* with high sensitivity and high specificity in order to rapidly and accurately diagnose *Ehrlichia canis* infection.

Another object of the present invention is to provide a kit for detecting *Ehrlichia canis* with high sensitivity and high specificity in order to rapidly and accurately diagnose *Ehrlichia canis* infection.

An additional object of the present invention is to provide a method for detecting *Ehrlichia canis* with high sensitivity and high specificity in order to rapidly and accurately diagnose *Ehrlichia canis* infection.

According to an aspect of the present invention, there is provided a primer pair for detecting *Ehrlichia canis*, comprising a forward primer having a sequence of 5'-ATTAATGTACTATGCTCCAAG-3' (SEQ ID NO: 1) and a reverse primer having a sequence of 5'-GTTGAGTTTCTTTCTTCTTTAG-3' (SEQ ID NO: 2). The forward primer and the reverse primer are used for real-time polymerase chain reaction.

According to another aspect of the present invention, there is provided a kit for detecting *Ehrlichia canis*, comprising a forward primer having a sequence of 5'-ATTAATGTACTATGCTCCAAG-3' (SEQ ID NO: 1), a reverse primer having a sequence of 5'-GTTGAGTTTCTTTCTTCTTTAG-3' (SEQ ID NO: 2) and a probe having a sequence of 5'-ACTATACAAGACGATAACACTGGTAGC-3' (SEQ ID NO: 3). The forward primer, the reverse primer and the probe are used for real-time polymerase chain reaction. The probe is labeled with a 5'-reporter dye and a 3'-quencher.

According to an additional aspect of the present invention, there is provided a method for detecting *Ehrlichia canis*, the method comprising amplifying nucleic acid from *Ehrlichia canis* using real-time polymerase chain reaction with a forward primer having a sequence of 5'-ATTAATGTACTATGCTCCAAG-3' (SEQ ID NO: 1), a reverse primer having a sequence of 5'-GTTGAGTTTCTTTCTTCTTTAG-3' (SEQ ID NO: 2) and a probe having a sequence of 5'-ACTATACAAGACGATAACACTGGTAGC-3' (SEQ ID NO: 3). The probe is labeled with a 5'-reporter dye and a 3'-quencher.

The above objects and advantages of the present invention become more readily apparent to those ordinarily skilled in the art after reviewing the following detailed description and accompanying drawings, in which:

BRIEF DESCRIPTION OF THE DRAWINGS

FIG. 1 shows the corresponding positions of the forward primer, the reverse primer and the probe on the sequence of the p30 gene;

FIG. 2 shows the DNA sequences of the forward primer, the reverse primer and the probe.

DETAILED DESCRIPTION OF THE PREFERRED EMBODIMENT

Figure 3A:
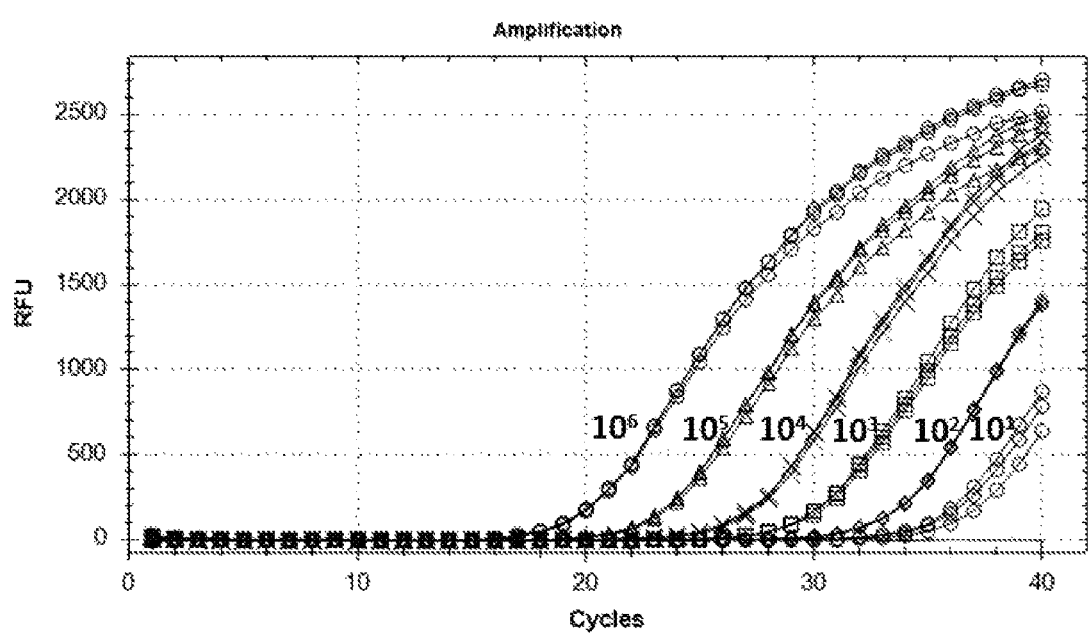
FIGS. 3A and 3B show the analysis of the amplification of the real-time PCR assay.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The present invention utilizes real-time polymerase chain reaction (Real-time PCR), also called quantitative polymerase chain reaction (Q-PCR), with probe-based detection for detecting *Ehrlichia canis*. In Real-time PCR, the specific forward and reverse primers and probe hybridize to the DNA target of *Ehrlichia canis*, wherein the probe is labeled with a 5'-reporter dye and a 3'-quencher. During PCR amplification, the probe is cleaved and the reporter dye and quencher are separated, so that the resulting increase in fluorescence can be detected. In an embodiment, the reporter dye is FAM fluorescence, and the quencher is BHQ1 group.

The DNA target for this assay is a variable region of the p30 gene (GenBank accession number: CP000107.1) that contains sequence that is species-specific for *Ehrlichia canis*. PCR primers and probe are designed using Primer3 and chosen on the basis of GC content and lack of hairpin structures. FIG. 1 shows the corresponding positions of the forward primer, the reverse primer and the probe on the sequence of the p30 gene (SEQ ID NO: 4). As shown in FIG. 1, the forward primer starts at position 42, the probe starts at position 79, and the reverse primer starts at position 182. This primers and probe combination is predicted to amplify the DNA of *Ehrlichia canis* strains with an amplicon size of 141-bp. FIG. 2 shows the DNA sequences of the forward primer, the reverse primer and the probe, wherein the forward primer (SEQ ID NO: 1) includes 21-mer, the reverse primer (SEQ ID NO: 2) includes 22-mer, and the probe (SEQ ID NO: 3) includes 27-mer.

To ascertain the specificity of the PCR primers and the probe for *Ehrlichia canis*, the primer pair, including the forward primer and the reverse primer, and the probe are checked by Primer-BLAST from NCBI, and the blast result shows that no other similar species have 100% same fragment compare to the primer pair and the probe of the present invention. The result demonstrates that the specificity of the primer pair and the probe is quite high, and the primer pair and the probe can be only used to amplify and detect the p30 gene of *Ehrlichia canis*.

Therefore, the present invention provides a primer pair for detecting *Ehrlichia canis*, comprising a forward primer having a sequence of 5'-ATTAATGTACTATGCTCCAAG-3' (SEQ ID NO: 1) and a reverse primer having a sequence of 5'-GTTGAGTTTCTTTCTTCTTTAG-3' (SEQ ID NO: 2). The present invention also provides a kit for detecting *Ehrlichia canis*, comprising a forward primer having a sequence of 5'-ATTAATGTACTATGCTCCAAG-3' (SEQ ID NO: 1), a reverse primer having a sequence of 5'-GTTGAGTTTCTTTCTTCTTTAG-3' (SEQ ID NO: 2) and a probe having a sequence of 5'-ACTATACAAGACGATAACACTGGTAGC-3' (SEQ ID NO: 3). On the other hand, the present invention also provides a method for detecting *Ehrlichia canis*, the method comprising amplifying nucleic acid from *Ehrlichia canis* using real-time polymerase chain reaction with a forward primer having a sequence of 5'-ATTAATGTACTATGCTCCAAG-3' (SEQ ID NO: 1), a reverse primer having a sequence of 5'-GTTGAGTTTCTTTCTTCTTTAG-3' (SEQ ID NO: 2) and a probe having a sequence of 5'-ACTATACAAGACGATAACACTGGTAGC-3' (SEQ ID NO: 3).

In some other embodiments, since the primer pair of the present invention is specific to *Ehrlichia canis*, all the sequence located between the forward primer and the reverse primer may be used as the probe sequence, and thus, the probe sequence is not limited to the aforesaid sequence. Further, the probe can be designed to hybridize to any strand of the DNA, so both the complementary sequences at the same location can be used as the probe sequence. Therefore, the complementary sequence of the aforesaid probe sequence may also be used as the probe sequence for detecting *Ehrlichia canis*.

The following describes an example of the method for detecting *Ehrlichia canis* of the present invention.

First, DNA is extracted from 200 μl of EDTA-preserved whole blood using the QIAamp DNA blood Mini kit for blood protocol (Qiagen) and eluted in 100 μl of elution buffer. Then the real-time PCR assay is performed on the Bio-Rad real-time PCR machine (CFX96). The PCR reaction mixture includes 10 μl of KAPA Fast probe universal master mix, 250 nM of forward and reverse primers and 250 nM of probe, wherein the forward primer has a sequence of 5'-ATTAATGTACTATGCTCCAAG-3' (SEQ ID NO: 1), the reverse primer has a sequence of 5'-GTTGAGTTTCTTTCTTCTTTAG-3' (SEQ ID NO: 2) and the probe has a sequence of 5'-ACTATACAAGACGATAACACTGGTAGC-3' (SEQ ID NO: 3). 3 μl extracted DNA template is added to each reaction in a total volume of 20 μl. Cycling conditions are as follows: 95° C. for 3 min, followed by 40 cycles of denaturation at 95° C. for 3 sec, and annealing/extension at 60° C. for 20 sec.

An *Ehrlichia canis*-positive control is constructed by cloning the partial p30 gene fragment into a vector (RBC Cloning System). A series of six 10-fold dilutions are prepared from this recombinant plasmid DNA (10, $10^2$, $10^3$, $10^4$, $10^5$ and $10^6$ copies/μl). The dilution series are analyzed in triplicate to determine the lower limit of *Ehrlichia canis* DNA detection and the linearity and efficiency of amplification of this real-time PCR assay.

Figure 3B:
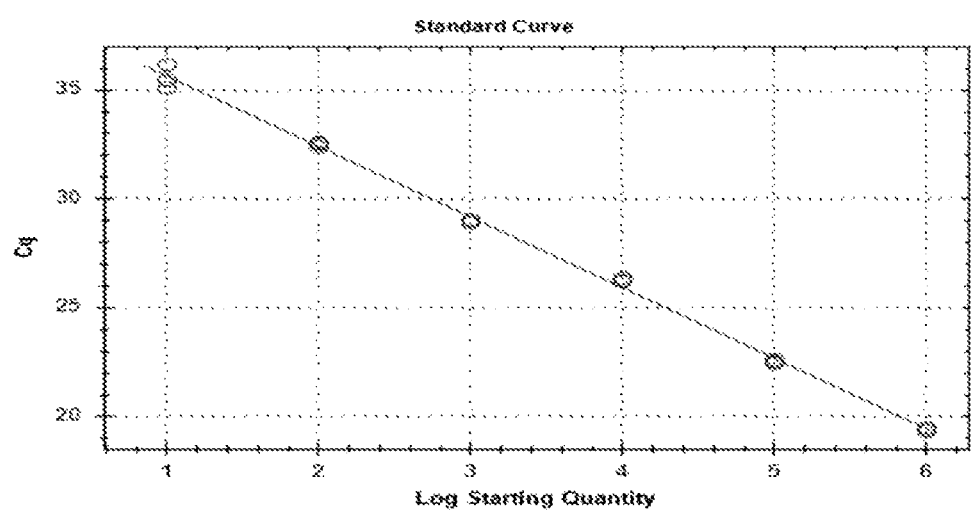

FIGS. 3A and 3B show the analysis of the amplification of the real-time PCR assay. FIG. 3A shows the amplification curve of different copies of plasmid samples, which reveals that the assay has high sensitivity. FIG. 3B shows the assay has good linearity with an $R^2$ of 0.998, which is very close to the theoretical optimum of 1.0. Therefore, the assay could be expanded as a quantitative assay to estimate gene copy number in clinical samples.

In conclusion, the present invention provides a method for detecting *Ehrlichia canis* using real-time PCR with specific primer pair and probe. The method of the present invention has advantage of high sensitivity, and should allow the detection of low *Ehrlichia canis* in subclinically infected cases. Moreover, diagnosis in early stage or acute phase is very critical for *Ehrlichia canis* treatment; some studies show that when dogs are treated in the acute phase of ehrlichiosis, they improve quickly, within 24-48 hours, and their prognosis is good when the whole courses of therapy are administered. The method of the present invention further has advantage of high specificity, which is able to specifically differentiate *Ehrlichia canis* from other tick-borne pathogens and is very helpful for vets to choose the optimal treatment program. In addition, in recurrent disease after treatment or failure after treatment, the method of the present invention could determine if the original diagnosis was incorrect, so as to reduce risk of transfusion transmission by testing blood donors.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for detecting *Ehrlichia canis*, the method comprising amplifying nucleic acid from *Ehrlichia canis* using real-time polymerase chain reaction with a forward primer consisting of a sequence of 5'-ATTAATGTACTAT-GCTCCAAG-3' (SEQ ID NO: 1) and a reverse primer consisting of a sequence of 5'-GTTGAGTTTCTTTCT-TCTTTAG-3' (SEQ ID NO: 2).

2. The method according to claim 1 wherein a probe consisting of a sequence of 5'-ACTATACAAGACGA-TAACACTGGTAGC-3' (SEQ ID NO: 3) is used for the real-time polymerase chain reaction.

3. The method according to claim 2 wherein the probe is labeled with a 5'-reporter dye and a 3'-quencher.

* * * * *

```
                             SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 1
attaatgtac tatgctccaa g                                              21

<210> SEQ ID NO 2
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 2
gttgagtttc tttcttcttt ag                                             22

<210> SEQ ID NO 3
<211> LENGTH: 27
<212> TYPE: DNA
<213> ORGANISM: Artificial Sequence
<220> FEATURE:
<223> OTHER INFORMATION: Synthetically generated probe

<400> SEQUENCE: 3
actatacaag acgataacac tggtagc                                        27

<210> SEQ ID NO 4
<211> LENGTH: 843
<212> TYPE: DNA
<213> ORGANISM: Ehrlichia Canis

<400> SEQUENCE: 4
atgaattgca aaaaattct tataacaact gcattaatgt cattaatgta ctatgctcca     60
agcatatctt tttctgatac tatacaagac gataacactg gtagcttcat catcagtgga   120
aaatatgtac caagtgtttc acattttggt gttttctcag ctaaagaaga aagaaactca   180
actgttggag tttttggatt aaaacatgat tggaatggag gtacaatatc taactcttct   240
ccagaaaata tattcacagt tcaaaattat tcgtttaaat acgaaaacaa cccattctta   300
gggtttgcag gagctattgg ttattcaatg ggtgggccaa gaatagaact tgaagttctg   360
tacgagacat tcgatgtgaa aaatcagaac aataattata agaacggcgc acacagatac   420
tgtgctttat ctcatcatag ttcagcaaca agcatgtcct ccgcaagtaa caaatttgtt   480
ttcttaaaaa atgaagggtt aattgactta tcatttatga taaatgcatg ctatgacata   540
ataattgaag gaatgccttt ttcaccttat atttgtgcag gtgttggtac tgatgttgtt   600
tccatgtttg aagctataaa tcctaaaatt tcttaccaag gaaaactagg attaggttat   660
agtataagtt cagaagcctc tgtttttatc ggtggacact ttcacagagt cataggtaat   720
```

-continued

```
gaatttagag acatccctgc tatggttcct agtggatcaa atcttccaga aaaccaattt    780
gcaatagtaa cactaaatgt gtgtcacttt ggtttagaac ttggaggaag atttaacttc    840
tga                                                                  843
```